United States Patent [19]
Zabetakis et al.

[11] Patent Number: 5,380,298
[45] Date of Patent: Jan. 10, 1995

[54] MEDICAL DEVICE WITH INFECTION PREVENTING FEATURE

[75] Inventors: Paul M. Zabetakis, Stamford, Conn.; Catherine M. Cotell, Alexandria, Va.; Douglas B. Chrisey, Bowie, Md.

[73] Assignee: The United States of America as represented by the Secretary of the Navy, Washington, D.C.

[21] Appl. No.: 43,914

[22] Filed: Apr. 7, 1993

[51] Int. Cl.$^6$ ............ A61M 5/32; A61M 25/00
[52] U.S. Cl. .................... 604/265; 604/280
[58] Field of Search ........... 604/265, 264, 280, 266, 604/27, 53, 171; 427/2; 424/682, 602, 618, 641; 128/DIG. 21; 623/11, 12, 16

[56] References Cited

U.S. PATENT DOCUMENTS

| | | | |
|---|---|---|---|
| 4,592,920 | 6/1986 | Murtfeldt | 427/2 |
| 4,847,163 | 7/1989 | Shimamura et al. | 428/469 |
| 5,151,122 | 9/1992 | Atsumi et al. | 106/35 |
| 5,242,706 | 9/1993 | Cotell et al. | 427/2 |

OTHER PUBLICATIONS

Aoki et al., "Sintered Hydroxyapatite for a Percutaneous Device and its Clinical Application," *Medical Progress through Technology*, 12, 1987, pp. 213–220.

Shin et al., "Surface Properties of Hydroxyapatite Ceramic as new Percutaneous Material in Skin Tissue," *Journal of Mateials Science: Materials in Medicine*, 3, 1992, pp. 219–221.

Kawahara et al., "J. Biom. Mat. Res.", vol. 14, 597–605, 1980.

Taniguchi et al., Jpn. J. Artif. Organs 20(2), 460–464, 1991.

Amano et al., Jpn. J. Artif. Organs 18(3), 1093–1096, 1989.

Amano et al., ASAIO Transactions 1990, 36: M494–M496.

Yoshiyama et al., "Peritoneal Dialysis International", vol. 11, Supplement 1, 1991, No. 297.

Zemel et al., Peritional Dialysis International, XII Annual CAPD Abstracts, 1992, No. 117.

Cotell et al., J. Appl. Biomaterials, vol. 3, pp. 87–83, 1992.

*Primary Examiner*—C. Fred Rosenbaum
*Assistant Examiner*—V. Alexander
*Attorney, Agent, or Firm*—Thomas E. McDonnell; Barry E. Edelberg

[57] ABSTRACT

A flexible medical device which is intended to be disposed in the opening or the incision in the skin tissue of an animal includes a thin, flexible, adherent film coating of a bioactive ceramic material at least at a point where the flexible portion of the medical device exits from the tissue. This bioactive coating bonds with the skin at the exit site to prevent infection of the tissue while allowing the catheter to remain flexible.

23 Claims, 4 Drawing Sheets

MEDICAL DEVICE WITH INFECTION PREVENTING FEATURE

BACKGROUND OF THE INVENTION

1. Field of Invention

This invention pertains to the field of medical devices and particularly to medical devices for insertion into and prolonged use in animals.

2. Description of the Background Art

Skin exit site infections are a major source of morbidity with all indwelling intra-abdominal and intravascular medical devices such as catheters. Made from a flexible polymeric material, such as silicone or polyurethane, these catheters, while being biocompatible, are associated with infections at the site where they exit from the skin. Despite attempts to minimize the risk of infection by the use of different techniques of catheter placement and modification of catheter design, exit site infections continue to be a problem with catheters indwelling for any prolonged period of time.

Since the skin is an efficient barrier to infection, it is not surprising that a break therein would lead to bacterial entry, especially of staphylococcus, streptococcus, and gram negative organisms. It is, therefore, curious to note that disruption of this barrier by teeth and horns is not associated with recurrent infection. Since hydroxylapatite (HA), the mineral component of teeth and horns, is known to be a bioactive ceramic, a skin-HA interface would possess properties that would minimize bacterial entry and infection.

An hydroxylapatite device comprising a rigid cylindrical portion coaxially attached to and extending normally from a rigid disc portion of larger diameter has been suggested. The rigid disc portion is subcutaneously implanted, with the cylindrical portion extending outside the patient. Typically, flexible catheter tubing is threaded through a hole extending along the central axis of the cylindrical and disc portions and then welded to the device. In use, the flexible catheter tubing extends into the body of a patient, thereby providing an indwelling catheter. Such a device has demonstrated excellent biocompatibility over periods of 6 to 28 months in several patients. A tight and sterile relationship between skin tissue and hydroxylapatite was observed. However, the design of that prior device implies severe restriction of patient mobility, partly because of the rigid cylindrical portion extending essentially perpendicularly from the patient.

SUMMARY OF THE INVENTION

An object of this invention is to reduce the occurrence of infections which have been associated with the use of an indwelling medical device which extends into and protrudes from the skin of an animal.

Another object of this invention is to permit reasonable mobility of an animal attached to an indwelling medical device while reducing the occurrence of infections.

Another object of this invention is to provide a tight and sterile relationship between skin tissue and an indwelling medical device without significantly reducing the mobility of the animal attached to that device.

These and other objects of this invention are realized by a medical device, especially a tubular catheter, having a coating, of thin cross-section, of a biocompatible and bioactive material on at least a flexible portion of its outer periphery. In use, the flexible medical device extends into and protrudes from a site in the skin of the animal. The device is constructed so that the coating is provided at least at the attachment site, i.e., where the flexible portion of the device extends into and protrudes from the animal's skin, during use.

Another aspect of the present invention concerns a method of catheterization using the device. A further aspect of the present invention concerns the provision of the medical device in sterile condition, in sterile packaging.

BRIEF DESCRIPTION OF DRAWINGS

A more complete appreciation of the invention will be readily obtained by reference to the following Description of the Preferred Embodiments and the accompanying illustrative drawings in which like numerals in different figures represent the same structures or elements, wherein.

DETAILED DESCRIPTION OF PREFERRED EMBODIMENT(S)

The medical device according to the present invention is intended to extend through and protrude from an attachment site in the skin of an animal, i.e., a site at which a portion of the medical device subtends the skin tissue. Another portion of the medical device is typically held at a point external to, and away from the body of the animal, i.e., distal to the attachment site. This holding point constitutes the external terminus of the device and is typically a fluid reservoir (either a source of, or drain for, fluid), such as an intravenous fluid bag. Alternatively, the holding point, which is at the external terminus of the device, could also be a site through which a wire, fiber, or probe may be inserted into the body of the animal through a hollow core of the medical device. The device includes a flexible member at least at a portion of which, in use, contacts the animal's tissue surrounding the attachment site This flexible member may be in fluid communication with the fluid reservoir.

Motion of the body at this attachment site tends to bend or flex this flexible member. Throughout this specification and the claims that follow, an element of the medical device is considered "flexible" if that element permits the portion of the body at the attachment site to essentially retain its mobility, i.e., if it does not significantly interfere with movement of the body about the attachment site. Within the context of the present specification and claims, the mobility of an attachment site is essentially retained if the attachment of the device to the attachment site does not significantly restrict the movement of the attachment site relative to the external terminus, except for unavoidable physical restrictions such as the limited length of the device and the mass of the device, etc. This flexibility simplifies examination of the attachment site and external terminus and enhances the comfort of the animal.

In order to reduce the likelihood of infection, at least the portion of the flexible member corresponding to the attachment site is coated and surrounded on at least a portion of its outer periphery with a continuous and adherent layer of biocompatible, bioactive ceramic material having a small cross-sectional thickness. The material is "bioactive" in that tissue surrounding the attachment site grows along, and bonds with, the material. As a result, that tissue develops a tight and sterile relationship with the coating. The occurrence of exit site infections is thereby reduced or eliminated. The material is "biocompatible" in that it does not cause any significant adverse reaction in the animal, i.e., it is biologically compatible.

The biocompatible, bioactive coating must have a thin cross-sectional thickness which is sufficiently small to maintain the flexibility of the flexible member and avoid unduly restricting the motion of the attached animal. To retain both flexibility and effectiveness in reducing or eliminating the occurrence of exit site infections, the coating must essentially retain its structural integrity and remain adherent to the flexible member during the bending associated with mobility of the attachment site. In other words, the coated portion of the flexible member must remain flexible. In the present specification and the appended claims, a coating "essentially retains its structural integrity and adherence to the flexible member upon bending" if enough of the coating for tissue growth and attachment thereto remains adhered to the flexible member to achieve the purposes of the present invention, e.g., to at least reduce the occurrence of infections that have been associated with the use of an indwelling medical device. Preferably, the coating can withstand bending, preferably radical bending, (i.e., crimping), to about 90° or more (e.g., 120°, 150° or even to a total crimping of 180°) of a flexible member onto which it has been coated, while essentially retaining its structural integrity and adherence to the flexible member. Thus, throughout the present specification and claims, a coating on the flexible member is deemed "flexible" if it permits the coated portion of a flexible member to remain flexible while essentially maintaining the coating's structural integrity and adherence to the flexible member.

Typically, the bioactive coating has a cross-sectional thickness of about 0.01 to about 5000 microns. Preferably, the bioactive coating has a cross-sectional thickness of no more than about 1000 microns. Most preferably, the bioactive coating has a cross-sectional thickness of about 0.05 to about 500 microns.

The medical device according to the present invention may be any medical device suitable for extending through and protruding outward from the skin tissue at a site in the body of an animal for prolonged periods. Typically, the device is a hollow tube such as a catheter. Most often, the device is a cylindrical hollow tube.

For the sake of convenience, an axis of the device that constitutes an axis along which the cross-section of the coating is taken will be referred to as a radial axis, i.e., an axis of thickness. An axis of the device that is perpendicular or essentially perpendicular to the radial axis and is along the length of the device will be referred to as a longitudinal axis, i.e., the axis of length. By way of example, for a device which is a hollow, tubular cylinder, a longitudinal axis corresponds to an element of the cylinder, and a radial axis corresponds to an axis along which a right section of the cylinder is taken. For a circular cylinder, all right sections are congruent.

The length of the coating along the flexible member of the device is not particularly critical. However, the coated section should be sufficiently long as to assure that the device may be readily inserted and fixed in position with the coating in contact with the tissue about the attachment site. Generally, the length of the coating on the flexible member is about 0.1-25 centimeters, preferably about 0.2-5 centimeters, and especially about 0.3-3 centimeters.

The device according to the present invention passes through an attachment site in the skin tissue. The opening or the incision can be made in any animal, such as a mammal, particularly a human being. Because the medical device of the present invention will usually be removable only by cutting the tissue which has bonded with the coating, the attachment site is preferably an artificial opening in the skin tissue. Although the present invention also contemplates the possibility of using the device in an opening which is naturally present (urinary tract, nasal passage, etc.), considerable postoperative discomfort might occur after removal of the device from such openings.

The bioactive and biocompatible coating may be applied to the flexible member by any method capable of providing a bioactive coating which is of sufficiently thin cross-section so as to be flexible as that termed is defined above. Preferably, the coating is provided as taught in U.S. Pat. No. 5,242,706, the entirety of which is incorporated herein by reference for all purposes. That patent, which names Catherine M. Cotell, Douglas B. Chrisey, Kenneth S. Grabowski and James A. Sprague as co-inventors, teaches a method and apparatus for depositing bioactive and biocompatible material onto a substrate by exposing the bioactive and biocompatible material (target) to a laser beam at a position adjacent to the substrate. Henceforth, the phrase "laser-deposited" is used to mean striking a target with a laser beam so that material is ablated from the target and deposited onto the substrate (see also, Cotell et al., "Pulsed Laser Deposition of Hydroxylapatite Thin Films on Ti-6Al-4V," J. Appl. Biomaterials, Vol. 3, pp 87–93 (1992), the entirety of which is incorporated herein by reference, for all purposes).

The bioactive and biocompatible coating material may generally comprise any suitable bioactive and biocompatible material. A preferred bioactive and biocompatible material is hydroxylapatite, the chemical formula of which is $Ca_{10}(PO_4)_6(OH)_2$. Other bioactive and biocompatible materials which may be used include HA-like phases (i.e., amorphous or crystalline calcium- and phosphorus-containing phases such as $\alpha$-tricalcium phosphate, $\beta$-tricalcium phosphate, tetracalcium phosphate), calcium oxide, $Ca_2P_2O_7$, natural bone, other bioceramics, for example, biologically active glasses, typically referred to as bioglasses, e.g., the compositions disclosed in U.S. Pat. Nos. 4,103,002, 4,159,358, 4,234,972, 4,478,904 and 4,775,646, the entire disclosures of which are incorporated herein by reference for all purposes, fluorapatite, and other bioactive and biocompatible materials. The bioactive and biocompatible material may comprise a single bioactive and biocompatible material or a mixture of bioactive and biocompatible materials. It is also possible to provide two or more distinct layers of the same or different biocompatible materials, i.e., multiple layers of biocompatible materials. In such cases, the outermost layer should be both bioactive and biocompatible.

The bioactive and biocompatible material (target) may generally be in any shape suitable for being exposed to a laser beam (for example, a pellet, disc, cylinder or sphere). The preferred condition of the bioactive and biocompatible material (target) is a dense pellet. A particularly preferred pellet diameter is about 0.75 inch. In the case of bioactive and biocompatible ceramics that may be delivered in the form of powders suspended in buffer solutions, such as hydroxylapatite, the powders may be dried in a vacuum oven and subsequently pressed into dense pellets. The preferred temperature range for the vacuum drying is less than 120° C. and the preferred range of pressures for the pressing procedure is 40,000–100,000 psi. The pellets may then be sintered, preferably in air or $O_2$, at a temperature preferably within the range of from 450° C. to 650° C. and cooled, preferably slowly, to room temperature.

The substrate for the deposition of the coating may be any material suitable for use as the flexible member of a flexible medical device for use as described above. All or part of the medical device may be flexible. Preferably, the flexible portion of the medical device extends for at least a length equal to that of the flexible coating thereon (which coating contacts the skin at the attachment site during use). The presence of the flexible coating on other portions of the medical device that are not flexible, although not deleterious to the present invention, will have little positive effect. Of course, the flexible portion of the medical device may be longer than the flexible coating, provided that during use, the flexible coating on the flexible portion contacts the attachment site. Typically, the substrate comprises a polymer selected from the group consisting of silicone, polyurethane, polyvinyl chloride and mixtures thereof. The substrate can generally be of any desired shape and orientation for the in-dwelling medical device. For instance, the shape can be regular (e.g., flat and planar, tubular) or irregular.

Any suitable laser source can be employed. In general, as discussed below, a short pulsed laser is particularly preferred for providing a coating on a medical device in accordance with the present invention. For example, an excimer laser (e.g., ArF, KrF, XeF or XeCl) can be used, a KrF excimer laser being especially preferred. Other short pulsed lasers, e.g., Nd—YAG or $CO_2$, could be used.

The bioactive and biocompatible material (target) being exposed to the laser beam and the substrate are preferably positioned within a chamber having an environment whose temperature, pressure and chemical composition are controlled. Suitable environments according to the method of U.S. Pat. No. 5,242,706 include argon/water, oxygen, and other reactive gas mixtures (for example, those having a partial pressure of oxygen such as carbon monoxide/carbon dioxide, hydrogen/water) as well as inert gases, such as argon. Two particularly preferred environments in accordance with the method of U.S. Pat. No. 5,242,706 are argon/water and oxygen. For creating an argon/water environment, there may be provided a gas inlet port which passes through a bubbler before passing into a vacuum chamber. For creating an oxygen environment, there may be provided a gas inlet port which passes directly into a vacuum chamber. The background pressure within the chamber during a deposition may be within the range of from about 0–760 Torr; 0.3 Torr is a particularly preferred total pressure.

The distance between the target and the substrate is preferably within the range of from about 3 centimeters to about 10 centimeters. A particularly preferred distance is about 4 centimeters. In general, larger distances are more suitable for deposition on larger substrate areas. Distances of greater than 10 centimeters may be used if desired, for example, for deposition on larger surface areas. The thickness of the deposited film will be proportional to the number of laser pulses to which the target is exposed.

The bioactive and biocompatible material (target) may be mounted on any support means suitable for supporting the bioactive and biocompatible material. In accordance with a preferred aspect of the method described in U.S. Pat. No. 5,242,706 the bioactive and biocompatible material (target) is mounted on a moving support means, such as a rotating and/or translating shaft, such that different portions of the target are in the center of the laser beam at different times, thereby extending the useful lifetime of the target and providing enhanced film uniformity. A preferred rate of rotation (and the rate employed in the Examples which follow herein) is about 0.5 revolution per second. Such an arrangement allows for greater uniformity of deposition on the substrate. Instead of (or in addition to) moving the bioactive and biocompatible material (target), the center of the laser beam could be moved to achieve similar effects. In general, larger areas may be coated by rastering the center of the laser beam across the target surface. In these cases, larger targets (diameters greater than 0.75 inch) would be preferred. In accordance with one modification according to the method described in U.S. Pat. No. 5,242,706, the substrate may be manipulated (e.g., rotated and/or translated) during deposition to allow deposition on non-planar or irregularly-shaped substrates.

In accordance with another preferred aspect of the method described in U.S. Pat. No. 5,242,706 the laser may be a pulsed laser (as mentioned above, short pulsed lasers are preferred according to the method of U.S. Pat. No. 5,242,706). Lasers for use in accordance with the method of U.S. Pat. No. 5,242,706 generally emit light having a wavelength in the range of from about 193 nanometers to about 1100 nanometers, an energy in the range of from about 0.1 to about 10 Joules/centimeter$^2$, a pulsewidth of from about $10^{-12}$ to about $10^{-6}$ second and a pulse repetition frequency of from about 0 to about 1000 Hertz. In general, energy density (fluence) affects morphology, that is, higher energies tend to produce deposited films which have larger particles and which are less dense. In the Examples which follow herein, the laser that was used emitted light having a wavelength of about 248 nanometers, an energy of about 250 millijoules/pulse, a pulsewidth of about 30 nanoseconds and a pulse repetition frequency of about 20 Hertz.

The laser deposition method and system described herein and in U.S. Pat. No. 5,242,706 have numerous advantages over prior methods and systems. For example, the method described in that application can be conducted at room temperature, if desired, thereby avoiding problems associated with oxidation of the substrate, degradation of the substrate or the film due to annealing and elimination of structural water, e.g., from hydroxylapatite. Also, the method described in that application can be conducted in a wide variety of gaseous environments, including water vapor environments. This feature lends a degree of control over the stoichiometry of the films. Operational parameters can be selected so as to (1) control whether a deposited film of bioactive and biocompatible material is amorphous, crystal-line, or a mixture of amorphous and crystalline phases, (2) control the crystal structure of the deposited film, (3) control the morphology of the deposited film, (4) achieve desired stoichiometry, e.g., the ratios of calcium to phosphorus in a deposited HA film and/or (5) provide better adhesion between the deposited film and the substrate. Moreover, for deposition of HA, operational parameters can be selected so as to control how much calcium phosphate (tricalcium phosphate or tetracalcium phosphate) is in a crystalline phase. Those operational parameters include the chemical makeup of the environment within the chamber, the pressure within the chamber and the temperature at the surface of the substrate. In addition, by selecting laser conditions (e.g., energy density, wavelength, pulse rate), target fabrication procedures (e.g., composition, density, sintering temperature) and/or by using ion beam-assisted pulsed laser deposition, one can control the porosity of the deposited film and enhance the adhesion of the film to the substrate. In particular, the deposition of hydroxylapatite, as opposed to anhydrous tricalcium phosphate, requires the presence of water within the deposition chamber.

In practicing the deposition method described in U.S. Pat. No. 5,242,706, using a hydroxylapatite target, the following relevant observations have been made:

(1) in any gas environment or an oxygen chamber environment at a total pressure of 300 mTorr, at temperatures below 400° C., the deposited films are generally amorphous, regardless of substrate;

(2) in an oxygen chamber environment at a pressure of 300 mTorr, at temperatures between 400° C. and 700° C., the deposited films generally include crystalline HA and α-tricalcium phosphate, whereas at temperatures greater than 700° C., the deposited films generally include crystalline HA and β-tricalcium phosphate;

(3) in an oxygen chamber environment, at a pressure less than or equal to 100 mTorr and a temperature of 600° C., the deposited films are generally amorphous;

(4) in an argon/water chamber environment, at a pressure of 300 mTorr, at temperatures between 400° and 700° C., the deposited films essentially consist of crystalline HA, whereas at temperatures greater than 700° C., the deposited films generally include crystalline HA and tetracalcium phosphate.

(5) in an oxygen chamber environment, the Ca/P ratio in deposited films tends to be higher at lower pressures;

(6) in an argon/water chamber environment, the Ca/P ratio in films deposited on Ti-6Al-4V or Si tends to be greater than the theoretical Ca/P ratio of HA;

(7) the presence of water vapor in the chamber environment generally enhances the likelihood of obtaining HA or the amount of HA; and (8) the adhesion of deposited films to substrates tends to be better when deposited in an argon/water chamber environment than when deposited in an oxygen chamber environment.

Favorable conditions for the pulsed laser deposition of calcium phosphate-based bioceramic materials from hydroxylapatite targets onto a substrate are summarized in Table 1 below:

TABLE 1

Favorable Conditions of Substrate Temperature and Gaseous Environment During Pulsed Laser Deposition for the Fabrication of Specific Calcium Phosphate-Based Bioceramics

| Desired Phase | Substrate Temperature ($T_{sub}$) | Gaseous Environment |
| --- | --- | --- |
| amorphous HA | $T_{sub} < 400°$ C. | any gas |
|  | $T_{sub} > 400°$ C. | non-reactive gas |
| crystalline HA | $400°$ C. $< T_{sub} < 700°$ C. | inert gas, water vapor |
| α-tricalcium phosphate | $400°$ C. $< T_{sub} < 700°$ C. | $O_2$ |
| β-tricalcium phosphate | $T_{sub} > 700°$ C. | $O_2$ |
| tetracalcium phosphate | $T_{sub} > 700°$ C. | inert gas, water vapor |

Figure 1A:
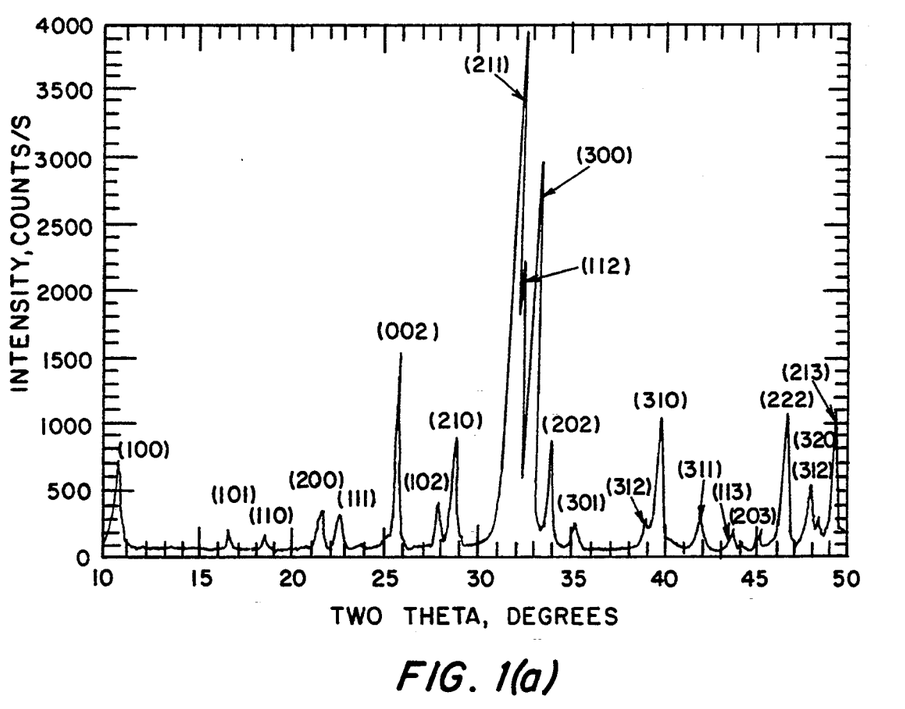
FIGS. 1(a) and 1(b) are X-ray diffraction patterns of (a) a pressed and sintered pellet of hydroxylapatite powder and (b) a thin coating of hydroxylapatite.
Figure 1B:
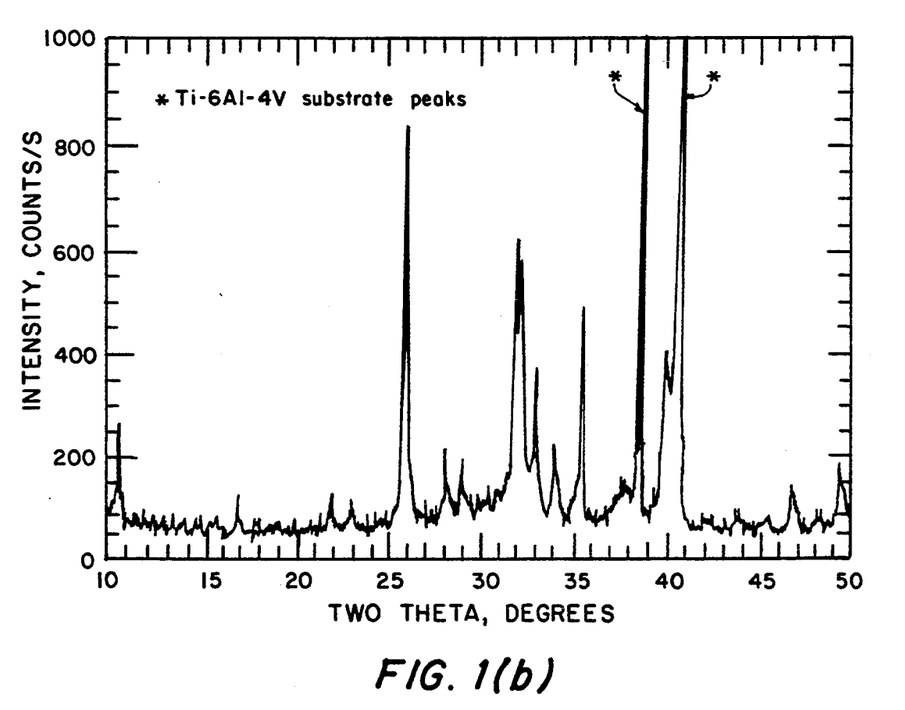

In one preferred embodiment, the bioactive coating of is crystalline hydroxylapatite. FIGS. 1(a) and 1(b) depict X-ray diffraction patterns from (a) a pressed and sintered pellet of crystalline hydroxylapatite powder and (b) an unannealed thin coating of hydroxylapatite deposited on a metal substrate by pulsed laser deposition at 500° C. in an argon-water vapor gas mixture at a total pressure of 0.3 Torr. The x-ray diffraction pattern in FIG. 1(b) shows clearly that the film deposited by pulsed laser deposition (PLD) was crystalline. Its x-ray diffraction pattern contained all the reflections from the standard HA powder pattern in FIG. 1(a). The only additional peaks found in FIG. 1(b) could be ascribed to the Ti-6Al-4V substrate on which the HA film was pulsed laser deposited. FIGS. 1(a) and 1(b) thus show successful direct deposition of thin coating of crystalline hydroxylapatite on a substrate.

Typically, films deposited at temperatures of less than about 400° C. are amorphous, especially in the case of hydroxylapatite. Higher temperatures are needed for crystallinity. Although optimal tissue attachment may occur for coatings that are crystalline, unfortunately, the materials typically used to form the flexible member of the medical device according to the present invention (e.g., silicone, polyurethane), onto which the coating is placed, will decompose at temperatures above about 200° C. To obtain crystalline coatings without heating the temperature sensitive substrates above about 200° C., the coatings may be annealed concurrently with growth by operating both an ablating laser beam and an annealing laser beam concurrently during deposition (i.e., in situ annealing), or by post-deposition laser annealing.

A preferred embodiment of the invention for temperature-sensitive catheter tubing or the like includes a bioactive amorphous hydroxylapatite coating deposited by pulsed laser deposition at a temperature within the range of room temperature to about 200° C. and subsequently laser annealed to crystallize the amorphous coating. As stated above, post-deposition laser annealing is an appropriate method to provide the film with sufficient heat for crystallization without heating the temperature sensitive substrate.

Figure 2A:
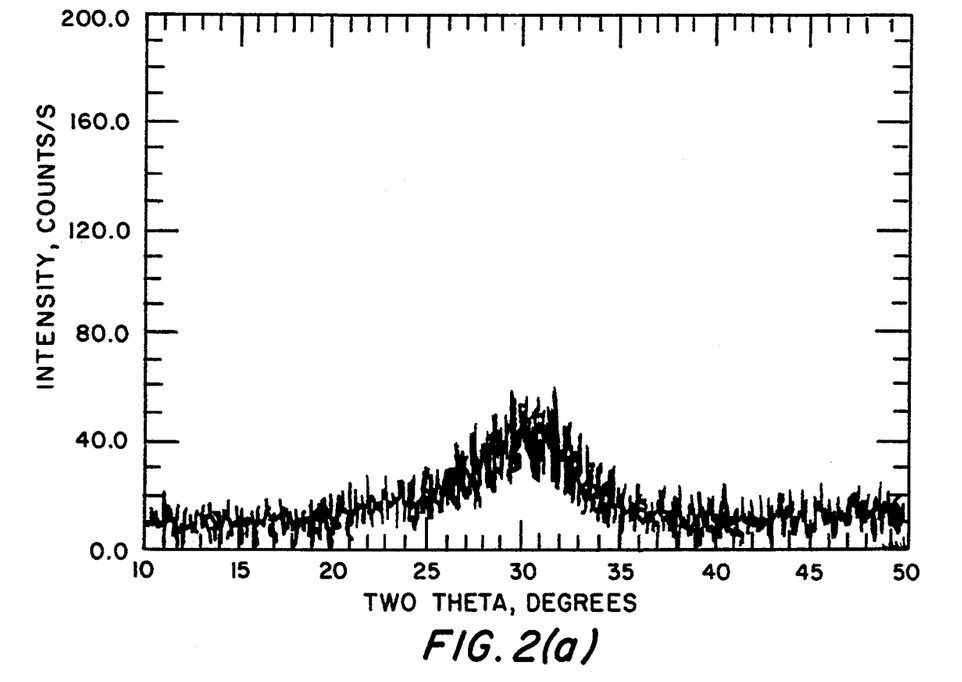
FIGS. 2(a) and 2(b) are X-ray diffraction patterns from coatings of hydroxylapatite deposited on a silicon (Si) substrate at room temperature in an argon-water vapor gas mixture at a total pressure of 0.3 Torr (a) as deposited and (b) after a laser anneal.
Figure 2B:
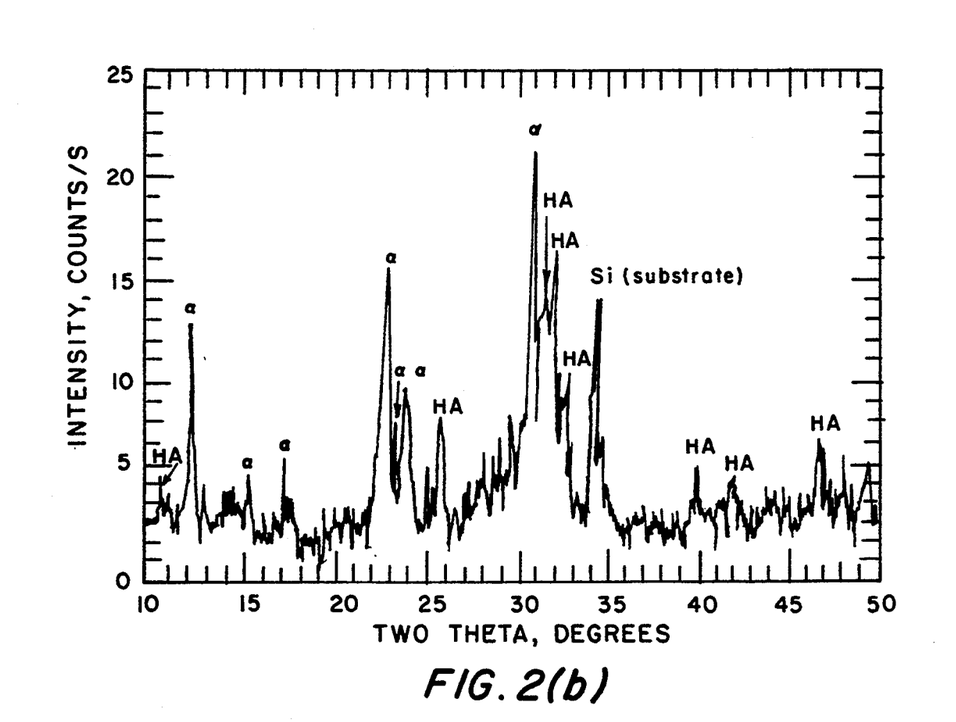

FIGS. 2(a) and 2(b) show X-ray diffraction patterns from coatings of hydroxylapatite deposited on a silicon substrate at room temperature in an argon-water vapor gas mixture at a total pressure of 0.3 Torr (a) as deposited and (b) after a laser anneal that resulted in crystallization of the amorphous coating in (a) to the mixture of crystalline hydroxylapatite (HA) and crystalline alpha tricalcium phosphate (α), shown in FIG. 2(b). The laser anneal is preferably accomplished at an energy density in the range of 0.001–0.5 Joules/centimeters$^2$, with 0.1–0.5 Joules/centimeter$^2$ being preferred, and with 0.1 to 0.2 Joules/centimeter$^2$ being a particularly preferred range of energy density. The laser anneal preferably consists of 1000–5000 shots at this energy density, with 2000 shots being a particularly preferred number. Any suitable laser source can be employed for the laser anneal. In general, a short, pulsed laser is particularly preferred in accordance with the present invention. For example, an excimer laser (e.g., ArF, KrF, XeF, or XeCl) can be used, a KrF excimer laser being particularly preferred. Other short pulse lasers, e.g., Nd—YAG or $CO_2$, can also be used.

In one embodiment of the present invention, the device may be a catheter. When the medical device according to the present invention is a catheter, it may be any type of catheter implanted for long term use through a cavity or an incision in living animal tissue. Examples of currently known catheters include surgical catheters, which can be non-manipulative, inflatable, and/or intravenous, intravascular catheter devices with and without inflatable portions, laser catheter systems, embolectomy catheters, dialysis catheters, percutaneous catheters, intrathecal catheters, and other catheters which are at least partially flexible.

Figure 3:
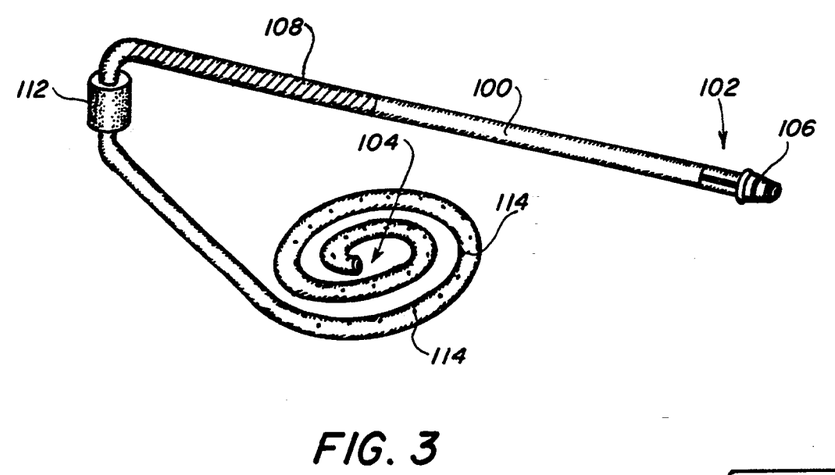
FIG. 3 is a perspective view of one embodiment of a flexible medical device according to the present invention, showing the location of the bioactive coating.

One particularly preferred percutaneous catheter according to the present invention is shown in FIG. 3. The particularities of catheter design are well-known in the art Nevertheless, some catheter specifications are provided here, in a non-limiting sense, as points of reference. The catheter shown in FIG. 3 is appropriate for peritoneal dialysis, for example.

Referring to FIG. 3, the catheter is composed of flexible silicone tubing 100, the outer end 102 protrudes outwardly from the body and the inner end 104 is disposed internally of the body. A coupling 106 is secured at the outer end of the catheter to which other devices 107 (FIG. 4) including fluid reservoirs, such as an intravenous fluid bag, can be connected, depending on the functionality of the catheter.

A preferred size of tubing 100 lies within the range of 0.01–1 centimeters in outer diameter and 0.001–1 centimeters in inner diameter. The total length of tubing 100 is preferably about 25–150 centimeters. As discussed above, bioactive coating 108 preferably extends longitudinally for preferably about 0.1–25 centimeters, more preferably about 0.2–5 centimeters, and especially about 0.3 to about 3 centimeters. In the case of a peritoneal dialysis catheter, the coating may be provided along the length of the catheter that runs from the rectus fascia to the exit site. The cross-sectional thickness of the bioactive coating is as discussed generally above.

In one specific embodiment, tubing 100 is 0.5 centimeters in outer diameter and 0.3 centimeters in inner diameter. The total length of the catheter tubing 100 is about 65 centimeters. At a distance of about 24 centimeters from outer end 102 is located the bioactive coating 108, of hydroxylapatite, in accordance with this invention. This bioactive coating is disposed circumferentially on the flexible tubing 0.6 centimeters in longitudinal extent and 1 micron in cross-sectional thickness. At a distance of about 36.5 centimeters from outer end 102 is located an internal cuff 112 composed of a porous material to allow fixation of the device in a patient by means of ingrowth of fibrous tissue into the pores. A particularly preferred material for the internal cuff is porous Dacron TM. The internal cuff 112 serves as a stabilizing means for the catheter within the tissue, but is not a required element of a catheter according to the present invention. At a distance of about 12 centimeters from the inner side of the internal cuff 112 is located a plurality of openings 114 to allow withdrawal or delivery of fluid through the catheter.

Figure 4:
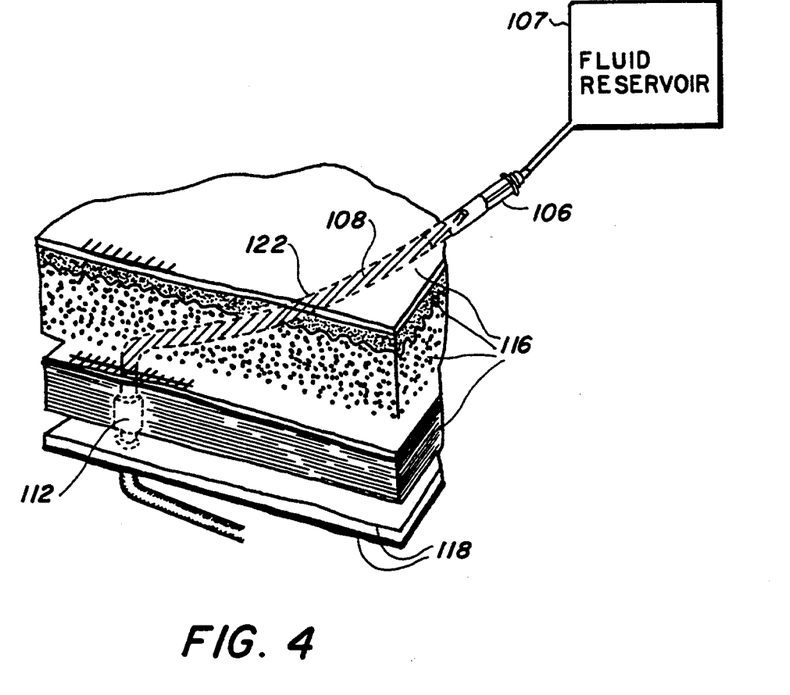
FIG. 4 is a perspective view of a portion of the flexible medical device of FIG. 3 having the bioactive coating in an operational disposition such that the bioactive coating is in tight, sterile contact with the skin where the catheter exits the body.

FIG. 4 shows a portion of the embodiment of FIG. 3 as it appears when inserted into the body of a human patient. Cuff 112 and the bioactive coating 108 are indicated on FIG. 4 disposed relative to the abdominal wall 116 and the parietal peritoneum layer 118. Abdominal wall 116 includes epidermis, subcutaneous, adipose, and rectus fascia layers. Bioactive coating 108 contacts the body at the attachment site.

Figure 5:
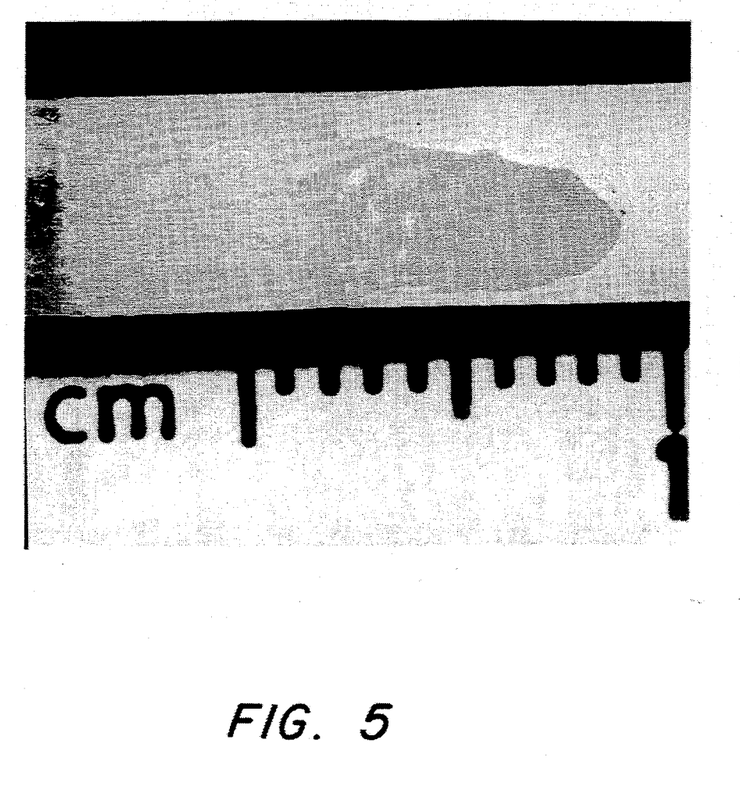
FIG. 5 is an optical micrograph of a piece of silicone catheter tubing coated with a thin film of hydroxylapatite by pulsed laser deposition.

FIG. 5 is an optical micrograph of a preferred bioactive coating of hydroxylapatite on a piece of flexible silicone tubing. Region (1) in the micrograph shows the uncoated tubing. In region (2), the tubing had been stretched over a support mount to prepare it for deposition. The diameter of the support exceeded the inner diameter of the catheter tubing, resulting in the coated tubing being put under compressive stress when it was removed from the mount after deposition. The compressive stresses resulted in spallation of the outer layer of coating as seen in region (2) extending into region (3), which did not experience the compressive stresses directly. The compressive stresses in region 2 resulted in spallation of the outer layer of hydroxylapatite from region (3) but a thin, inner layer of hydroxylapatite remained adherent. This inner layer remained adherent while radically bending through 90°. The bending process resulted in cracks due to the compressive stresses imposed during the bending. These cracks can be seen in region (3) oriented perpendicularly to the cracks in region (2), since the compressive stresses were applied from different directions. (The parts of the film placed under tension by these bending forces, i.e., the surface of the coating facing away from the direction of bending, did not crack.) Despite the spallation of the outer layer, the inner layer of the film remained sufficiently adherent for tissue attachment to be anticipated.

By providing a biocompatible and bioactive coating between the tissue and at at least a segment of the medical device at the point where the medical device exits the tissue (i.e., the attachment site), growth of healthy tissue around the medical device is promoted. Growth of infection-causing bacteria, which is facilitated by the oxygen in the environment, is prevented by the tight and sterile relationship between the medical device and the skin at the attachment site that results from the presence of the biocompatible and bioactive coating on the device.

The medical device contemplated herein is flexible at least at a portion which contacts the attachment site in use, and is intended to remain implanted in the animal for a long term. That term may be only one day or may be at least as long as that period during which infection at the attachment site would typically develop in the absence of the biocompatible and bioactive coating.

Obviously, many modifications and variations of the present invention are possible in light of the above teachings, and are intended to be encompassed within the scope of the appended claims. It should also be understood that, within the scope of the appended claims, the invention may be practiced otherwise than as specifically described.

What is claimed is:

1. A medical device having a section for insertion into and protrusion from an attachment site, surrounded by tissue, in a body of an animal, said section comprising a flexible member having an outer periphery; and a continuous, bioactive, biocompatible, flexible ceramic coating surrounding and adhered to at least a portion of said outer periphery of said flexible member, said coating having the ability to support growth of said tissue therealong and the ability to form a tight and sterile bond with said tissue, said flexible coating being sufficiently flexible so that said flexible member, when inserted into and protruding from said attachment site, does not significantly restrict movement of the body around said attachment site.

2. A medical device according to claim 1, further comprising a fluid reservoir located outside of said body in fluid communication with said flexible portion of said medical device.

3. The medical device of claim 1, wherein said coated portion of said flexible member can be radically bent to an angle of at least 90° while said coating essentially retains structural integrity and adherence to said flexible member.

4. The medical device of claim 3, wherein said flexible member comprises a polymeric material.

5. The medical device of claim 4, wherein said coating comprises at least one amorphous or crystalline material selected from the group consisting of hydroxylapatite, $\alpha$-tricalcium phosphate, $\beta$-tricalcium phosphate, tetracalcium phosphate, calcium oxide, $Ca_2P_2O_7$, fluorapatite, bioglasses and natural bone, and wherein said polymeric material comprises a polymer selected from the group consisting of silicone, polyurethane, polyvinyl chloride and mixtures thereof.

6. The medical device of claim 1, wherein the cross-sectional thickness of said coating is less than or equal to about 500 microns.

7. The medical device of claim 1, wherein said medical device is sterile.

8. The medical device of claim 1, wherein said flexible member comprises a conduit for conveying fluids to or from a mammal.

9. The medical device of claim 8, wherein said conduit comprises a hollow tube.

10. A catheter having a section for insertion into and protrusion from an attachment site, surrounded by tissue, in a body of an animal, said section comprising:

a flexible member having an outer periphery; and a continuous, bioactive, biocompatible flexible ceramic coating surrounding and adhered to at least a portion of said outer periphery of said flexible member, said coating having the ability to support growth of said tissue therealong and the ability to form a tight and sterile bond with said tissue, said flexible coating being sufficiently flexible so that said flexible member, when inserted into and protruding from said attachment site, does not significantly restrict movement of the body around said attachment site.

11. The catheter of claim 10, wherein said coated portion of said flexible member can be radically bent to an angle of at least 90° while said coating essentially retains structural integrity and adherence to said flexible member.

12. The catheter of claim 11, wherein said flexible member comprises a polymeric material.

13. The catheter of claim 12, wherein said coating comprises at least one amorphous or crystalline material selected from the group consisting of hydroxylapatite, $\alpha$-tricalcium phosphate, $\beta$-tricalcium phosphate, tetracalcium phosphate, calcium oxide, $Ca_2P_2O_7$, fluorapatite, bioglasses and natural bone, and wherein said polymeric material comprises a polymer selected from the group consisting of silicone, polyurethane, polyvinyl chloride and mixtures thereof.

14. The catheter of claim 10, wherein the cross-sectional thickness of said coating is less than or equal to about 500 microns.

15. An indwelling catheter, in situ, which extends into a body of a mammal having skin through an attachment site, surrounded by tissue, in said mammal's skin, said catheter comprising:

a flexible member having an outer periphery and a continuous, bioactive, biocompatible, flexible ceramic coating surrounding and adhered to said outer periphery of said flexible member at a portion of said catheter that contacts said skin at said attachment site, said coating having the ability to support growth of said tissue therealong and the ability to form a tight and sterile bond with said tissue, said flexible coating being sufficiently flexible so that said flexible member does not significantly restrict movement of the body around said attachment site.

16. The indwelling catheter of claim 15, wherein said coated portion of said flexible member can be radically bent to an angle of at least 90° while said coating essentially retains structural integrity and adherence to said flexible member.

17. The indwelling catheter of claim 16, wherein said flexible member comprises a polymeric material.

18. The indwelling catheter of claim 17, wherein said coating comprises at least one amorphous or crystalline material selected from the group consisting of hydroxylapatite, $\alpha$-tricalcium phosphate, $\beta$-tricalcium phosphate, tetracalcium phosphate, calcium oxide, $Ca_2P_2O_7$, fluorapatite, bioglasses and natural bone, and wherein said polymeric material comprises a polymer selected from the group consisting of silicone, polyurethane, polyvinyl chloride and mixtures thereof.

19. The indwelling catheter of claim 15, wherein the cross-sectional thickness of said coating is less than or equal to about 500 microns.

20. A method of catheterizing a mammal, comprising the steps of:

inserting through an attachment site, surrounded by tissue, in a body of a mammal, a catheter including:

a flexible member having an outer periphery; and a continuous, bioactive, biocompatible, flexible ceramic coating surrounding and adhered to at least a portion of said outer periphery of said flexible member, said coating having the ability to support growth of said tissue therealong and the ability to form a tight and sterile bond with said tissue, said flexible coating being sufficiently flexible so that said flexible member does not significantly restrict movement of the body around said attachment site.

21. The method of claim 20, further comprising the step of fixing said catheter to said mammal so that said flexible coating on said flexible member remains in contact with said attachment site.

22. The method of claim 21, wherein said mammal is a human.

23. A medical device having a section for insertion into and protrusion from an attachment site, surrounded by tissue, in a body of an animal, said section comprising:

a flexible member having an outer periphery; and a continuous, bioactive, biocompatible, flexible ceramic coating adhered to at least a portion of said outer periphery of said flexible member, said coating having the ability to support growth of said tissue therealong and the ability to form a tight and sterile bond with said tissue, said flexible coating being sufficiently flexible so that said coated portion, when bound to said tissue surrounding said attachment site, does not significantly restrict movement of the body around said attachment site.

* * * * *